United States Patent [19]

Robbins

[11] Patent Number: 5,050,425
[45] Date of Patent: Sep. 24, 1991

[54] APPARATUS AND METHOD FOR MEASURING VOLATILE CONSTITUENTS IN EARTH SAMPLES

[75] Inventor: Gary A. Robbins, Manchester, Conn.
[73] Assignee: University of Connecticut, Storrs, Conn.
[21] Appl. No.: 444,517
[22] Filed: Dec. 1, 1989
[51] Int. Cl.[5] ..................... G01N 33/18; G01N 33/24
[52] U.S. Cl. .................................. 73/19.1; 73/864.85
[58] Field of Search ................... 73/19.1, 19.01–19.09, 73/19.11, 19.12, 863.85, 863.86, 864.85, 864.91

[56] References Cited

U.S. PATENT DOCUMENTS

| | | | |
|---|---|---|---|
| 3,150,516 | 9/1964 | Linnenbom et al. | 73/19.1 |
| 3,768,302 | 10/1973 | Barringer | 73/28.01 |
| 3,934,453 | 1/1976 | Hessen | 73/19.11 |
| 4,112,736 | 9/1978 | Wheldon et al. | 73/31.04 |
| 4,585,060 | 4/1986 | Bernardin et al. | 73/864.34 X |
| 4,709,577 | 12/1987 | Thompson | 73/49.2 T X |

FOREIGN PATENT DOCUMENTS 1488535  6/1989  U.S.S.R. ................................. 73/19.1

OTHER PUBLICATIONS

Robbins et al., "Use of Headspace Sampling Techniques in the Field to Quantify Levels of Gasoline Contamination in Soil and Ground Water", Proceedings of NWWA/API Conf. on Petroleum Hydrocarbons and Organic Chemicals in Ground Water, Houston, Texas, Nov. 17–19, 1987, pp. 307–315.
Tchobanoglous, "Water Quality" (Book) pp. 122–123 Addison–Wesley, 1985.
Mackay et al., "Rate of Evaporation of Low-Solubility Contaminants from Water Bodies to Atmosphere", Environmental Science & Technology, vol. 9, No. 19, 1975, pp. 1178–1180.
Drozd et al., "Headspace Determination of Benzene in Gas–Aqueous Liquid System by the Standard Additions Method, Journal of Chromatography", 152, 1978, pp. 55–61.
Leighton et al., "Distribution Coefficients of Chlorinated Hydrocarbons in Dilute Air–Water Systems for Groundwater Contamination Applications", J. Chem. Eng. Data, 26, 1981, pp. 382–385.
Griffith et al., "A New Method for Field Analysis of Soils Contaminated with Aromatic Hydrocarbon Compounds", Proceedings of Conference on Eastern Regional Ground Water Issues, Sep. 27 ∝ 29, 1988, pp. 223–248.
Stolyarov, "Headspace Gas Chromatographic Determination of Aromatic Hydrocarbons in Natural And Waste Water", Chromatographia vol. 14, No. 12., Dec. 1981, pp. 699–703.
Gossett, "Measurement of Henry's Law Constants for $C_1$ and $C_2$ Chlorinated Hydrocarbons", Environ. Sci. Technol. vol. 21, No. 2, 1987, pp. 202–208.
Robbins et al., "A Field Screening Method for Gasoline Contamination Using A Polyethylene Bag Sampling System", GWMR, Fall, 1989, pp. 87–97, (Oct. 12).
Holbrook, "Hydrocarbon Vapor Plume Definition Using Ambient Temperature Headspace Analysis", Proceedings of NWWA/API Conf. on Petroleum Hydrocarbons and Organic Chemicals in Ground Water, Houston, Texas, Nov. 17–19, 1987, pp. 317–328.

*Primary Examiner*—Tom Noland
*Attorney, Agent, or Firm*—Martin Novack

[57] ABSTRACT

The disclosure is directed to an apparatus and method for measuring the presence of a volatile constituent of a sample of ground water or soil mixed with water. In an embodiment of the apparatus, a valve system is provided, and has a plurality of branches. A reclosable and collapsible bag, preferably of the polyethylene freezer bag type, is provided for receiving the sample. The bag has a hole in a wall thereof, preferably near the top of the bag. A gasketed fitting is provided for air-tight coupling a first of the branches of the valve system to the bag via the hole. A detector of the volatile constituent is coupleable to a second of the branches of the valve system. The valve system is operative, in one position thereof, to close off the first branch so as to isolate the bag, and in another position thereof, to couple the first and second branches so that the detector can communicate with the bag. In a disclosed embodiment, the valve system has a third branch coupled to ambient air, and the valve system is operative in said "one" position thereof to couple the second and third branches and close off the first branch, and is operative in said "another" position thereof to couple the first and second branches and close off the third branch.

15 Claims, 1 Drawing Sheet

APPARATUS AND METHOD FOR MEASURING VOLATILE CONSTITUENTS IN EARTH SAMPLES

BACKGROUND OF THE INVENTION

This invention relates to techniques for testing earth samples and, more particularly, to an apparatus and method for measuring volatile constituents in a sample of ground water or soil mixed with water. The invention was supported by the U.S. Environmental Protection Agency, and the U.S. Government has certain rights in the invention.

The leakage of underground storage tanks, and other types of pollution which introduce hydrocarbons and other volatile contaminants into the ground, has become a serious problem in many places. Recent federal, state and local regulations have or will soon require that investigations be conducted to determine whether underground gasoline storage tanks have leaked. An integral part of these investigations is determining whether soil or ground water in the vicinity of tanks have been contaminated. This is generally accomplished by the use of soil/gas surveying, drilling to collect soil samples, and construction of monitoring wells to collect ground water samples. Of significance are the more soluble and easier to detect components of gasoline, such as benzene, toluene, ethylbenzene and the xylenes. Samples are generally analyzed in the laboratory by gas chromatography or gas chromatography/mass spectrometry for volatiles and semi-volatiles using a number of known methods. Given the relatively high costs for these analyses, field screening can be conducted to select samples for laboratory evaluation. Also, field screening is used to guide investigations in terms of the depth and lateral extent of drilling. Additionally, field screening may be employed in guiding remediation by excavation. An evaluation of some existing field screening techniques, particularly those using so-called "headspace sampling", are described in "Use Of Headspace Sampling Techniques In The Field To Quantify Levels Of Gasoline Contamination In Soil And Ground Water", G. A. Robbins et al., Proc. of NWWA/API, Nov. 1987.

Headspace sampling techniques involve placing a consistent volume or weight of ground water or soil mixed with water in a container, sealing the container, agitating, allowing time to permit volatile constituents to be released into the air headspace of the container, and then using a detector to measure the volatile constituent in the headspace. Existing headspace sampling techniques have various disadvantages and limitations, and it is among the objects of the invention to provide an improved headspace sampling apparatus and method.

SUMMARY OF THE INVENTION

The present invention is directed to an apparatus and method for measuring the presence of a volatile constituent of a sample of ground water or soil mixed with water. In accordance with an embodiment of the apparatus of the invention, a valve system is provided, and has a plurality of branches. A reclosable and collapsible bag, preferably of the polyethylene freezer bag type, is provided for receiving the sample. The bag has a hole in a wall thereof, preferably near the top of the bag. Means are provided for air-tight coupling a first of the branches of the valve system to the bag via the hole. A detector of the volatile constituent is coupleable to a second of the branches of the valve system. The valve system is operative, in one position thereof, to close off the first branch so as to isolate the bag, and in another position thereof, to couple the first and second branches so that the detector can communicate with the bag.

In the preferred embodiment of the invention, the valve system has a third branch coupled to ambient air, and the valve system is operative in said "one" position thereof to couple the second and third branches and close off the first branch, and is operative in said "another" position thereof to couple the first and second branches and close off the third branch.

An embodiment of the method of the invention includes the following steps: coupling a reclosable and collapsible polyethylene bag to the first branch by connecting the branch to a hole in a wall of the bag; introducing the sample into the bag through the reclosable opening thereof, and sealing the reclosable opening of the bag; with the valve system in its "another" position, pumping air into the bag by attaching an air pump to the second branch; with the valve system in its "one" position, agitating the bag and its contents to induce the release of the volatile constituent into the air headspace above the sample; with the valve system in its "another" position and the first branch in ambient air, coupling the detector to the second branch; switching the valve system to its "one" position so that the detector communicates with the headspace in the bag; and reading the detector to obtain a measure of the volatile constituent in the headspace.

The apparatus and method hereof have substantial advantages over techniques which employ no valve or other types of valves which employ a glass or rigid plastic container for receiving the sample. The reclosable and collapsible polyethylene bag used in the present invention has a readily testable and reliable seal which is easy to open and close. The bag is inexpensive and conveniently disposable. This is in contrast to other containers which must be carefully cleaned before reuse in order to ensure against contamination of subsequently tested samples. A further important advantage is the collapsibility of the bag which maintains the equalization of pressure in the bag headspace at about atmospheric pressure. Also, the valve system permits the detector to communicate with ambient air while it is being connected and before it is switched to communication with the headspace air. These features facilitates more reliable and consistent testing, and avoid curtailment of the detector instrument's flow rate. A still further benefit of the bag used herein is its flexibility, which permits disaggregation of the sample by squeezing the bag.

Further features and advantages of the invention will become more readily apparent from the following detailed description when taken in conjunction with the accompanying drawing.

BRIEF DESCRIPTION OF THE DRAWING

The drawing shows a schematic diagram of an apparatus in accordance with an embodiment of the invention and which can be used to practice an embodiment of the method of the invention.

DESCRIPTION OF THE PREFERRED EMBODIMENT

Figure 1:
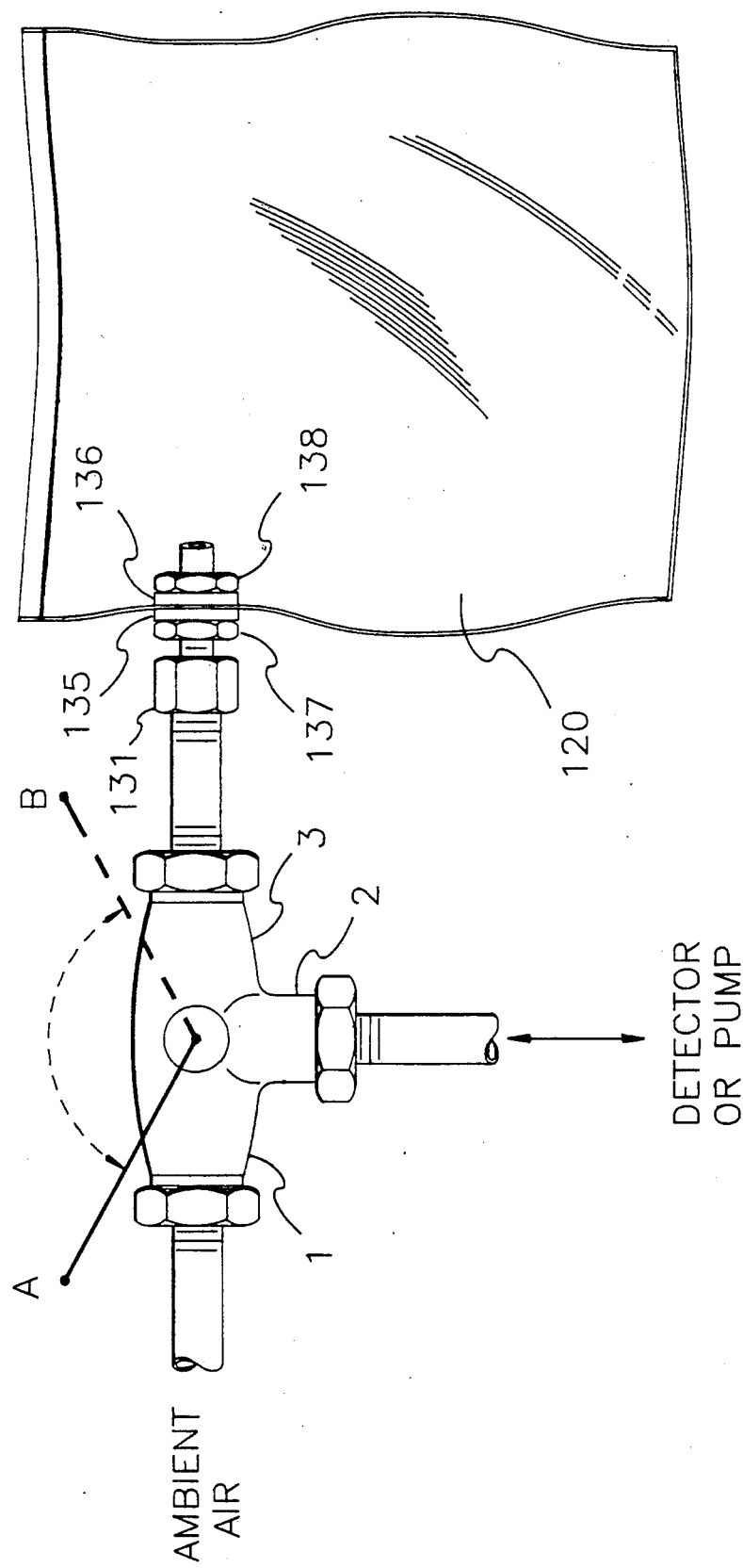

Referring to FIG. 1, there is shown a diagram of a reclosable bag sampling system in accordance with an embodiment of the invention. A reclosable polyethylene freezer bag 120 (such as of the type made and sold by Dow Chemical as "Ziploc") is connected to a three-way valve system 150. In an operating embodiment, the reclosable polyethylene bag 120 was a one-quart bag, and the three-way valve system 150 was a so-called 3-way ball valve of a type sold by Imperial Eastman, Inc., No. 108-HD. The valve 150 has three branches labeled 1, 2, and 3, respectively, one manually adjustable position that can be referred to as position A, and a second manually adjustable position that can be referred to as position B. In position A, the branch 2 is coupled to the branch 1 (i.e., these branches are permitted to communicate with each other), and the branch 3 is closed off. In position B, the branch 2 is coupled to the branch 3, and the branch 1 is closed off. In the present embodiment, the bag 120 is connected to the valve system through a hole in the bag which can be made with a standard hole punch. A connector fitting, for example a ⅛ inch NPT connector fitting 131 coupled to the valve branch 3, is inserted through the hole, and the fitting is sealed to the bag using gaskets 135, 136 and the nuts 137, 138 on respective sides of the hole. Other suitable seals can also be employed. Using a hand pump on branch 2, and with the valve in the B position, the bag 120 can be filled until just taut and tested for leakage. If bag leakage is observed, a different bag is attached.

If proven leak-tight, the reclosable seam of the bag 120 is opened. A sample (e.g. an aqueous sample or a soil sample mixed with distilled water) can then be introduced into the bag through the opening. A volumetric flask can be used for liquid samples, and a predetermined volume (e.g. using a spoon) or weight can be used for soil samples. The bag is then sealed and inflated until just taut, again using a hand pump with the valve in the B position. The bag is isolated, by placing the valve in position A (which closes off branch 3) and then agitated. This can be done by hand, using a rocking motion. The agitation tends to release vapor into the headspace, either directly from an aqueous sample in which it was initially contained, or from soil into water and then into the headspace. The flexibility of the bag also has the advantage of permitting disaggregation of the sample by hand, if desired, by squeezing the bag and its contents. This will accelerate the release of vapors from the sample.

After a sample is agitated, headspace concentration measurement can be implemented by coupling a detector to branch 3 and, at the desired time or times, moving the valve to position B. The 3-way valve is seen to allow the detector to draw ambient air prior to sample measurement (i.e., via branch 1), and permits rapid switching to the headspace of the bag (i.e., by switching to valve position B) in a manner that does not curtail the instrument's flow rate. The vapors evolved in the headspace can be measured in a manner not affected by inducing a vacuum while the detection instrument draws air from the bag; i.e., as the air is drawn out of the bag into the sampling instrument, the bag collapses and thus maintains an internal pressure of about one atmosphere. In one example, tests were conducted using a flame ionization detector ("FID") that was calibrated with a methane in air standard. In another example, tests were conducted using a photoionization detector ("PID") that was calibrated with an isobutylene in air standard. It will be understood, however, that any suitable type of detector can be employed.

Following each analysis the bag and its contents should be properly disposed. If appropriate, the gaskets can be re-used. For example, it has been found that buna-n gaskets used as a seal on the bag can be re-used without sample carry-over. The valve system can be purged by pumping air through the system. The effectiveness of purging can be checked by connecting the valve system to the measuring instrument.

Consider measuring the concentration of a single volatile constituent in a sample of air that is contained within a chemically inert and collapsible bag. The bag is connected to a PID or FID, as described above. As the instrument withdraws air from the bag during sampling, the bag collapses and maintains a constant internal pressure. Therefore, the concentration measured may be equated to the actual concentration by $$C_{mi} = R_i C_i, \qquad (1)$$

where $C_{mi}$ equals the measured vapor concentration for a constituent i, $C_i$ equals the actual vapor concentration, and $R_i$ is a response factor. The response factor will depend on the instrument's sensitivity to constituent i relative to a calibration gas and to a given set of calibration conditions. Pertinent calibration conditions would include the condition of the instrument and its detector, whether the instrument's response is being affected by quenching, and whether the actual concentration levels are within the linear range of the instrument. If measurements are performed on a series of air samples containing a single constituent i, Equation (1) predicts that measured and actual concentrations will be linearly related providing $R_i$ remains constant.

Expanding Equation (1) for the case where multiple vapor constituents are present in the bag results in $$C_{mT} = \sum_{i=1}^{n} C_{mi} = \sum_{i=1}^{n} (R_i C_i) = \sum_{i=1}^{n} (R_i C_i / C_T) C_T \qquad (2)$$

where $C_{mT}$ is the measured total concentration, $C_T$ is the actual total concentration, and n is the total number of constituents. Equation (2) predicts that measured and actual total concentrations will be linearly proportional among samples, if the following conditions hold. The $R_i$ value for each constituent remains constant among samples, and either a constituent's concentration varies, or the concentration of all constituents vary in proportion (i.e., $C_i/C_T$ remains constant for each constituent) from sample to sample.

Next, consider sealing a water sample, containing a single, dissolved, volatile constituent, into a bag inflated with clean air. With time, the constituent will volatilize into the headspace. If the sample is well agitated and the volume of headspace remains constant, the measured headspace concentration at any time may be described by a first order transfer function expressed as $$C_{mi}(t) = R_i C_i(t) = R_i C_{ie}[1 - \exp(-k_i t)] \qquad (3)$$

where $C_{mi}(t)$ and $C_i(t)$ are the measured and actual vapor concentrations at time t, respectively, $C_{ie}$ is the actual equilibrium headspace concentration, and $k_i$ is an effective mass transfer coefficient [se Tchobanoglous et al., 1985]. Equation (3) predicts an exponential achievement of an equilibrium concentration with time that depends on the magnitude of the mass transfer coefficient. The mass transfer coefficient is a function of the individual constituent, temperature, degree of sample agitation, and the contact area between the water and the headspace. Mass transfer coefficients for commonly found volatile contaminants tend to be relatively large [see Mackay et al., 1975]. In well-agitated headspace vessels, vapor concentration equilibrium has been reported to occur within minutes [see, for example, Drozd et al., 1978; Leighton et al., 1981; Griffith et al., 1988].

The equilibrium headspace concentration in Equation (3) may be related to the equilibrium water concentration by Henry's law, expressed as $$C_{ie} = H_i C_{iwe} \quad (4)$$

where $H_i$ is a dimensionless Henry's law constant and $C_{iwe}$ is the equilibrium concentration in the water, expressed in the same dimensional units are the vapor concentration. Based on mass continuity and the previously developed equations, the measured equilibrium headspace concentration may be related to the initial dissolved concentration of the constituent by $$C_{mie} = R_i C_{ie} = R_i H_i C_{iwe} = [R_i/(1/H_i + V_{hs}/V_w)] C_{iwo} \quad (5)$$

where $V_{hs}$ is the volume of headspace, $V_w$ is the volume of water sample added to the bag, and $C_{iwo}$ is the initial concentration of the dissolved volatile constituent. Various forms of Equation (5) have been used in conducting head-space analysis in gas chromatography [see, for example, Stolyarov, 1981 or Gossett, 1987]. The equation indicates that for a single volatile constituent the measured headspace concentration will be linearly proportional to the initial water concentration. In order for this linearity to hold with respect to a series of samples, $R_i$, $H_i$ and $V_{hs}/V_w$ must remain constant. Because $H_i$ is a function of temperature and water quality factors (e.g., salinity), these conditions must be kept constant to maintain linearity. However, Equation (5) predicts that the magnitude of non-linear effects will depend on the magnitude of $1/H_i$ relative to $V_{hs}/V_w$, the sensitivity of $H_i$ to temperature and water quality variations, and the degree to which these conditions vary among samples.

The preceding equations can be readily expanded by summation to treat multiple constituents, as in the case of expanding Equation (1) to Equation (2). Linearity between total equilibrium headspace concentration and total aqueous concentration will depend on the same factors mentioned previously. In addition, it will depend on the achievement of equilibrium headspace concentrations by all constituents at the time of measurement.

The effectiveness of partitioning aromatic compounds from soil into the headspace of VOA vial by agitation in water has previously been demonstrated [see Griffith et al., 1988]. Once constituents were partitioned from the soil, headspace equilibrium was shown to be described by the preceding theory for water-headspace partitioning. For a single constituent i, equilibrium partitioning among the three phases may be described by $$m_{iso} = m_{ise} + m_{iwe} = m_{ie} \quad (6)$$

where $m_{iso}$ is the mass originally on the soil sample, and $m_{ise}$, $m_{iwe}$, and $m_{ie}$ are the masses at equilibrium distributed among the soil, water and headspace, respectively. By performing appropriate substitutions of concentration and volume terms for mass terms, and by incorporating the previously cited equations, Equation (6) may be re-expressed as $$C_{mie} = R_i C_{ie} = R_i \{[M_s/V_w]/[((K_{isw}+1)-/H_i) + V_{hs}/V_w]\} C_{is} \quad (7)$$

where $M_s$ is the mass of soil added to the bag, $K_{isw}$ is a soil/water partition coefficient for constituent i, and $C_{is}$ is the concentration of the constituent on the soil on a mass/mass basis. As with the other equations, providing that the terms to the left of $C_{is}$ are kept constant among samples, the measured headspace concentration is predicted to be a linear function of the soil concentration.

As in the previous developments, Equation 7 can be readily expanded for the multiple constituent case. Again, linearity between measured total headspace and total soil concentration will depend on the extent to which the parameters previously cited remain constant from sample to sample.

For further details, reference can be made to "A field Screening Method for Gasoline Contamination Using A Polyethylene Bag Sampling System", G. Robbins et al., Fall 1989 GWMR. It will be understood that the interpretation of the detector measurements, and the underlying theory thereof are known in the art and are not, of themselves, inventive features hereof.

The invention has been described with reference to a particular preferred embodiment, but variations within the spirit and scope of the invention will occur to those skilled in the art. For example, it will be understood that other valve systems can be employed which achieve the same functions as those described herein or which have additional branches for separate connection of air pump and detector.

I claim:

1. Apparatus for measuring the presence of a volatile constituent of a sample of ground water or soil mixed with water, comprising:
    a valve system having a plurality of branches;
    a reclosable and collapsible bag for receiving said sample, said bag having a hole in a wall thereof;
    means for air-tight coupling a first of said branches to said bag via said hole;
    a detector of said volatile constituent coupleable to a second of said branches of said valve system;
    said valve system being operative, in one position thereof, to close off said first branch so as to isolate said bag, and in another position thereof, to couple said first and second branches so that said detector can communicate with said bag.

2. Apparatus as defined by claim 1, wherein said bag is a polyethylene bag.

3. Apparatus as defined by claim 2, wherein said valve system has a third branch coupled to ambient air, and wherein said valve system is operative in said one position thereof to couple said second and third branches and close off said first branch, and is operative in said another position thereof to couple said first and second branches and close off said third branch.

4. Apparatus as defined by claim 3, wherein said means for air tight coupling said first branch to said bag comprises a seal formed at the junction between said bag and said first branch.

5. Apparatus as defined by claim 2, wherein said means for air tight coupling said first branch to said bag comprises a seal formed at the junction between said bag and said first branch.

6. Apparatus as defined by claim 2, wherein said detector is an ionization detector.

7. Apparatus as defined by claim 1, wherein said valve system has a third branch coupled to ambient air, and wherein said valve system is operative in said one position thereof to couple said second and third branches and close off said first branch, and is operative in said another position thereof to couple said first and second branches and close off said third branch.

8. Apparatus as defined by claim 1, wherein said means for air tight coupling said first branch to said bag comprises a seal formed at the junction between said bag and said first branch.

9. For use in conjunction with a detector which can detect the presence of a volatile constituent from a sample of ground water or soil mixed with water, an apparatus comprising:
a valve system having a plurality of branches;
a reclosable and collapsible bag for receiving said sample, said bag having a hole in a wall thereof;
means for air-tight coupling a first of said branches to said bag via said hole;
said detector being coupled to a second of said branches of said valve system;
said valve system being operative, in one position thereof, to close off said first branch so as to isolate said bag, and in another position thereof, to couple said first and second branches so that said detector can communicate with said bag.

10. Apparatus as defined by claim 9, wherein said bag is a polyethylene bag.

11. Apparatus as defined by claim 1, wherein said valve system has a third branch coupled to ambient air, and wherein said valve system is operative in said one position thereof to couple said second and third branches and close off said first branch, and is operative in said another position thereof to couple said first and second branches and close off said third branch.

12. Apparatus as defined by claim 11, wherein said means for air tight coupling said first branch to said bag comprises a seal formed at the junction between said bag and said first branch.

13. Apparatus as defined by claim 10, wherein said means for air tight coupling said first branch to said bag comprises a seal formed at the junction between said bag and said first branch.

14. Apparatus as defined by claim 9, wherein said valve system has a third branch coupled to ambient air, and wherein said valve system is operative in said one position thereof to couple said second and third branches and close off said first branch, and is operative in said another position thereof to couple said first and second branches and close off said third branch.

15. Apparatus as defined by claim 9, wherein said means for air tight coupling said first branch to said bag comprises a seal formed at the junction between said bag and said first branch.

* * * * *